US006620186B2

(12) United States Patent
Saphon et al.

(10) Patent No.: US 6,620,186 B2
(45) Date of Patent: Sep. 16, 2003

(54) METHOD AND SYSTEM FOR MEDICAL LEAD IMPEDANCE TEST

(75) Inventors: Remy Saphon, Billancourt (FR); Gerard Taroni, Lissess (FR); Christophe Degardin, Villabe (FR)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/681,618

(22) Filed: May 10, 2001

(65) Prior Publication Data

US 2003/0036772 A1 Feb. 20, 2003

(30) Foreign Application Priority Data

May 25, 2000 (EP) .............................. 00480046

(51) Int. Cl.[7] ................................. A61N 1/08
(52) U.S. Cl. .................... 607/1; 607/27; 607/8; 607/116; 607/28
(58) Field of Search .................. 607/8, 27–29, 607/62, 116, 118, 4, 5, 1, 9

(56) References Cited

U.S. PATENT DOCUMENTS

| 4,140,131 | A | | 2/1979 | Dutcher et al. ........ 128/419 PT |
| 4,949,720 | A | | 8/1990 | Thompson ............. 128/419 P |
| 4,958,632 | A | * | 9/1990 | Duggan ...................... 607/11 |
| 5,201,865 | A | * | 4/1993 | Kuehn .......................... 607/8 |
| 5,431,687 | A | * | 7/1995 | Kroll ............................ 607/8 |
| 5,549,646 | A | * | 8/1996 | Katz et al. .................... 607/8 |
| 5,716,381 | A | * | 2/1998 | Reggiardo .................... 607/8 |
| 5,891,179 | A | | 4/1999 | Er et al. ...................... 607/27 |
| 6,104,954 | A | * | 8/2000 | Blunsden ...................... 607/8 |

* cited by examiner

*Primary Examiner*—Carl Layno
(74) *Attorney, Agent, or Firm*—Derek S. Jennings

(57) ABSTRACT

An apparatus for testing the impedance of a medical lead connecting an implantable stimulation device to a nerve or a muscle. The implantable device is of the type comprising a capacitor for stimulating the nerve or the muscle. The system of the invention comprises a current generator for generating a testing current "I" during a calibrated testing pulse and a power circuit coupled to the capacitor and to the current generator for determining if the capacitor is charged by the testing current during the calibrated testing pulse.

9 Claims, 4 Drawing Sheets

METHOD AND SYSTEM FOR MEDICAL LEAD IMPEDANCE TEST

BACKGROUND OF INVENTION

1. Technical Field

The present invention relates to medical implantable devices and more particularly to the test of medical lead impedance of implantable neurostimulators used for paraplegic people.

2. Background Art

It is a reality that either for natural reasons or consecutively to a malady or a traumatism, nerves or muscles of the human body may be affected and suffer from lack of stimulation or at least from a deficient stimulation. Electronic solutions to replace such deficiencies use Functional Electrical Stimulation devices (FES). State of the art of such devices mainly address the crucial problem of the heart attack with the well-known pacemakers. However, another important concern in which research of implantable solution is very active is the paraplegia domain in which the muscles are inert due to spinal injury.

Contrary to some devices like pacemakers which run continuously and need real time measurements, the implantable devices for paraplegic alternate active and inactive time periods which offer room for different measurements. Furthermore, as the generation of human walking is a complex algorithm, a great number of medical leads are used at the same time to activate the muscles of the inactivated legs (typically 16 or more leads are used as compared to two leads for cardiac pacemaker). In case some of the leads break, the device may be still active, and it is less vital that a real time integrity measurement be made for paraplegia devices than for pacemakers. Therefore, implantable devices for paraplegic do not need to be tested in real time, and checking can be done either at the system setup or during an active stimulation.

Generally, an implantable device performs two main functions: stimulation and telemetry. The stimulation is obtained by the generation of electrical pulses in order to deliver a current through a network of electrodes and medical leads in contact with the part of the body to be stimulated (muscle or nerve). The telemetry function is a feedback operation which allows to get information onto the integrity of the implantable device, such as measuring the level of power supply of the component or testing the value of the lead impedance formed by the association of the stimulated tissue plus the electrode in contact with it plus the wire connecting the electrode to the implantable device.

A first problem arises when the network of electrodes is placed within the body of a patient because several damages may affect the integrity of the leads such as partial or a total fracture in the electrical wires. However, the leads may be tested during the surgical operation which is not the purpose of the present invention.

Moreover, such kind of injury and others such as fibrosis may also appear during the time period the patient is using the stimulation system. It is therefore mandatory that these elements be tested regularly to be sure that stimulation pulses are sent with efficiency. Because of the non-accessibility of the F.E.S. device which is embedded within the patient body, the testing of the components is not easy. However, the testing of lead impedance has been addressed in many patents and only a few are described immediately hereinafter.

U.S. Pat. No. 4,949,720 discloses an apparatus for measuring the lead impedance in a pacemaker. The invention includes a large number of FET transistors operated in parallel to discharge a capacitor though the heart tissue. Pacer lead current is monitored by measuring the current through a small number of these transistors. The current monitoring function is performed by a current-to-voltage converter coupled to an analog-to-digital converter which may make one or more voltage measurements during the output pulse.

U.S. Pat. No. 4,140,131 disclose an apparatus for stimulating body tissue and in particular the heart, as including a device or circuit responsive to the initiation of stimulation and/or to the failure or pending failure of a component of the stimulating apparatus to provide the patient with a perceivable stimulation to a second, different portion of body tissue. There is disclosed an impedance level detector for sensing the impedance presented between the outputs of the stimulation apparatus to provide a warning signal indicating that the output impedance falls outside a predetermined range. In particular, the impedance level detector output is sensed by stimulation control logic to apply a first train of pulses at a first rate to an auxiliary electrode for stimulating the second portion of tissue. Further, there is included a voltage level detector for sensing when the power source voltage depletes below a predetermined level, to actuate the stimulation control logic to provide a second train of warning pulses to the auxiliary electrode, at a second, different rate than that of the first train. In this fashion, the patient not only is warned as to the pending failure or failure of a component of his pacemaker, but also is able to identify the failing component.

With these solutions, either the voltage (V) or the current (I) are measured across the lead impedance (R) and the final value of the impedance is obtained by computing the well-known Ohm's equation: V=R×I.

Another approach to determine the integrity of the leads consists in measuring a stimulation capacitor voltage and to deduce the impedance lead value from a well-known general equation:

$$V = V0 \times e^{(-T/RC)},$$

wherein V0 is the initial voltage of the stimulation capacitor and (1/RC) is the time constant. Such method is illustrated in the two following patents: In U.S. Pat. No. 5,891,179 from Er et al., a real-time impedance monitoring system is provided for use with an implantable medical device having an implantable electrical lead. The impedance monitoring system includes components for determining the electrical impedance of the lead as a function of time, with the determination being made substantially in real-time, and components for graphically displaying the electrical impedance of the lead as a function of time, with the display also being generated substantially in real-time.

In U.S. Pat. No. 5,201,865 from Kuehn, a method and apparatus for measuring lead impedance during pre selected test mode operation of an implantable body tissue stimulator is presented. Analysis circuitry is periodically triggered into operation, such as on each reprogramming by the physician or periodically as a function of elapsed time or number of stimulation events counted from the preceding measurement. The actual lead impedance, measured from the output circuit from the body tissue-stimulator pulse generator, and taking into account impedance of the interconnection between the lead connector pin and the pulse generator connector block, the lead electrical conductor and its connections with the electrode and the connector pin and the electrode-tissue interface, is calculated as a function of the ratio of the elapsed times that it takes to discharge a capacitor from a first reference voltage to a second reference voltage through a precision resistor and through the lead impedance itself. The calculated lead impedance may be stored in memory with a suitable time tag, employed to automatically effect a change in operating modes or change a lead and electrode selection, if measured lead impedance falls outside normal high and low impedance boundary values. In the pacing context, calculated lead impedance may be employed to adjust sense amplifier sensitivity and pacing output pulse parameters. The method and apparatus may also be employed to calculate cardioversion/ defibrillation lead impedance through selective partial discharge of high voltage output capacitors.

The '179 solution implies that the voltage measurement be picked at the end of the impedance path and thus that an extra-wire from the implant is required. Then, in case of paraplegia where a great number of electrodes are required, such solution is not acceptable due to the number of extra-wires that would be required.

Furthermore, in paraplegic application, the leads are not necessarily proximate to the FES device and the wiring may be long and difficult to access, thereby rejecting a solution as the aforementioned one.

In the '865 patent, the reader may assume that all the circuitry is powered with a unique common voltage VDD. In the case a high power voltage (i.e. 40 volts) is used for the stimulation capacitor and a lower voltage (5 volts) is used for the rest of the circuitry, this prior art solution is not acceptable as such because the circuitry must be adapted.

An important constraint of paraplegia is the need of interconnection of low powered components (the implant is powered less than 5 v) with high power output stages (high voltage over 40V and high current over 20 mA) which are needed for the stimulations.

Therefore, even if the cited pacemakers solutions are convenient for the measurement of lead impedance in the cardiology context, none of the aforementioned patents offers a complete solution for testing the functionality of leads impedance in paraplegic implantable device.

Thus, there is still a need for a simple, short time functional testing solution for paraplegic implantable stimulator.

SUMMARY OF INVENTION

It is therefore a feature of the present invention to provide an apparatus for testing the impedance of a medical lead connecting an implantable stimulation device to a nerve or a muscle. The implantable device is of the type comprising a capacitor for stimulating the nerve or the muscle. The system of the invention comprises a current generator for generating a testing current "I" during a calibrated testing pulse and a power circuit coupled to the capacitor and to the current generator for determining if the capacitor is charged by the testing current during the calibrated testing pulse.

Various other objects, features, and attendant advantages of the present invention will become more fully appreciated as the same becomes better understood when considered in conjunction with the accompanying drawings, in which like reference characters designate the same or similar parts throughout the several views.

DETAILED DESCRIPTION

In a preferred embodiment, the current generator comprises a pulse generator for generating the calibrated testing pulse. According to the type of test, i.e. the test of a nerve or of a muscle, a respective resistive path allows to maintain an adapted voltage at the output of the pulse generator.

A determination device preferably in the form of a power transistor is base-connected to the output of the pulse generator. A measure of the voltage resulting at the emitter point of the power transistor is made to determine if the testing current is provided by the collector path of the transistor or by the base path. If the tested channel is connected, the testing current flows from the high voltage of the muscle or nerve to the current generator, thereby charging the stimulation capacitor. In case the tested channel is disconnected, the current sunk by the current generator must be provided by one of the resistive path, thereby generating a characteristic voltage drop at the output of the pulse generator. The chosen voltage drops are such that no stimulation may be applied to the muscle or nerve.

Figure 1:
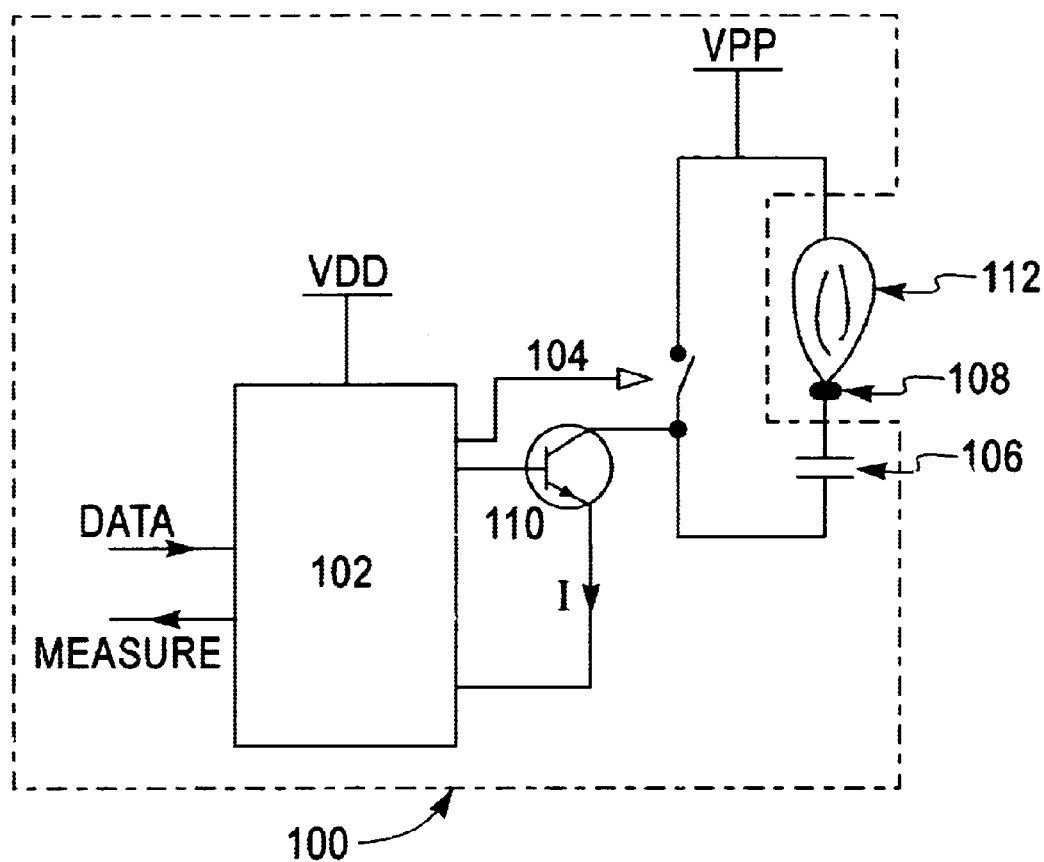
FIG. 1 shows an implantable FES using the circuit of the present invention.

Referring to FIG. 1, an exemplary implantable device 100 to be implanted in a paraplegic patient is described. To the extent that certain components of device 100 are conventional for stimulation application in their design and operation, such components (a conventional programmer for example) will not be described here and only the circuits operating in conjunction with the present invention are now described. The implantable device 100 comprises an Application Specific Integrated Circuit (generally ASIC) 102 powered at a VDD voltage. The ASIC to be detailed later receives input data on a "DATA" line from external circuitry to be operated either for stimulation or for measurements. The measured data are outputted on a "MEASURE" line. A controllable switch component having a command line 104 allows to discharge a stimulation capacitor 106 after each stimulation operation. The stimulation capacitor 106 is connected between an electrode 108 and a power transistor 110 in which flows a stimulation current I. The electrode 108 is connected to a muscle 112. It is to be understood that the electrode could be connected to a nerve for neural stimulation. As already explained, muscle and neural stimulation for paraplegia require a high power voltage VPP due to the intrinsic impedance of the muscle or the nerve.

Figure 2:
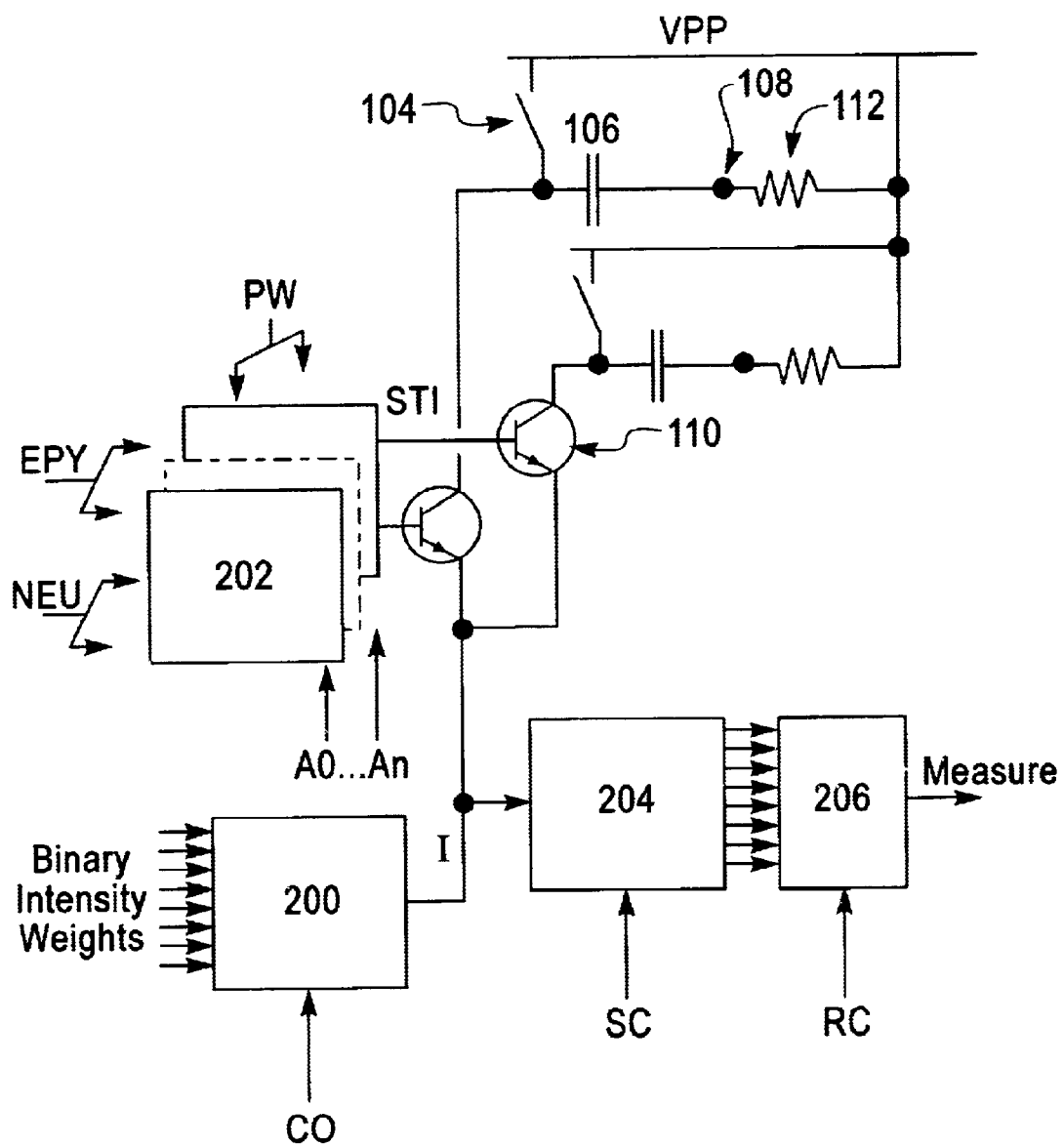
FIG. 2 shows a general block diagram of the relevant circuits of the present invention.

The details of the relevant circuits which make up the testing device of the present invention are shown in block circuit form in FIG. 2 with reference numerals being the same for circuits identical to FIG. 1. For sake of clarity, only two electrodes are shown on the figure but one of ordinary skill could easily extend the concept of the invention to a plurality of electrodes either connected to muscle or nerve.

A first Digital to Analog current converter 200 provides a first programmable calibrated stimulation current "I" to feed epymisial channels, depending on the value of intensity weights on the D/A converter input. A second Digital to Analog current converter (not shown for clarity reason) provides a second programmable calibrated stimulation current to feed neural channels. Each DAC may be conventional n-bits converter. Both DACs may be respectively activated by a command signal "CO" which enables the stimulation current "I" to be sunk only when the input data (the binary intensity weights) have reached stable values. In the preferred embodiment, the first DAC 200 is a 8-bits converter for muscle stimulation while the second DAC is a 6-bits converter for neural stimulation, and the stimulation current I1 is in the range of 0 to 25 mA for the epymisial case while the stimulation current I2 is in the range of 0 to 3 mA for the neural case.

A control circuit 202 inputting epymisial and neural selection signals "EPY" and "NEU" is coupled to power transistor 110. Preferably, one control circuit is associated to each electrode 108 and one circuit is active at a time. The selection of the active control circuit may be realized by common address decoding circuits (illustrated as address bits A0–An on FIG. 2). In response to a pulsed input signal "PW", control circuit 202 generates a calibrated command stimulation signal "STI" on base of power transistor 110.

Figure 3:
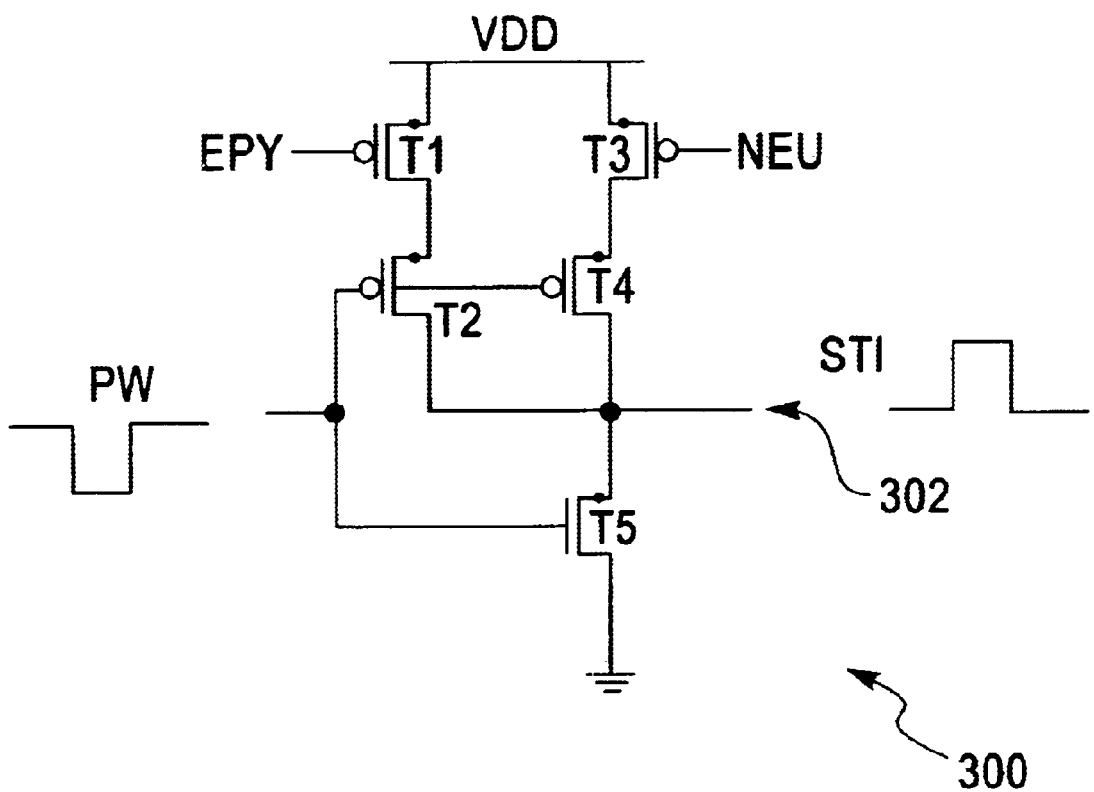
FIG. 3 shows a preferred implementation of control circuit of the present invention.

One preferred implementation of control circuit 202 is shown on FIG. 3, with circuit 300 being composed of five transistors of FET type. However, the person skilled in the art will easily devise other circuit design required by other technology such as bipolar transistors for example. Transistor T1 receives on its gate the "EPY" signal and having its drain connected to power voltage VDD. Similarly transistor T3 receives on its gate the "NEU" signal and having its drain connected to power voltage VDD. The source of T1 is connected to the drain of transistor T2. The source of T3 is connected to the drain of transistor T4. Transistors T2 and T4 are gate connected to receive the pulsed command signal "PW". The sources of T2 and T4 are connected to the drain of transistor T5 which also inputs on its gate pulsed command signal "PW". The source of T5 is connected to low voltage (ground voltage VG). The output "STI" of control circuit 300 is available on the output line 302.

During testing operation, a pulse signal "PW" is applied to the gate of transistors (T2,T4) to turn them ON and to the gate of transistor T5 to turn OFF. According to the active selection signal "EPY" or "NEU", one of the transistor T1 or T3 is ON, which means testing of a nerve channel or a muscle channel. The initial high voltage (VDD) on output line 302 is lowered by the voltage drop due to the resistive path made by either T1 and T2 or by T3 and T4. If there is no electrical discontinuity in the tested channel, the voltage on output line 302 (i.e. the base voltage of power transistor 110) remains high, and the current sunk in the emitter of power transistor 110 is provided by the collector of this latter. If there is an electrical discontinuity in the tested channel, the voltage on output line 302 decreases significantly as the current sunk in the emitter of transistor 110 is provided by the resistive path of control circuit 300 through the base of power transistor 110. The value of each resistive path is chosen such that the current for epymisial testing or neural testing allows a significant voltage drop while avoiding a stimulation effect of the nerve or muscle.

In the preferred implementation, for a power voltage VDD of 5V, the voltage drop is around 2V with a current of 2 mA for epymisial testing and a current of 200 uA for neural testing.

Coming back to FIG. 2, the circuits to measure the voltage on the emitter of power transistor 110 will now be described.

A voltage Analog to Digital Converter 204 is connected to the emitter of power transistor 110. A sampling clock signal "SC" is applied to the input of the converter 204 to sample the voltage of the emitter. The voltage is converted in a well-known manner into parallel bits. The parallel bits are stored in a register circuit 206. Register 206 is a common shift register which swaps the parallel bits into serial bits. The serial bits are outputted at a predetermined cycle time defined by a register clock "RC".

In an alternate embodiment, a selector circuit may be connected between the emitter of transistor 110 and A/D converter 204 in order to sample other analog data such as battery voltage level, power supplies measurement. A selector signal can be easily designed by a person skilled in the art to determine the selected type of data to be measured.

On top of FIG. 2, an electrical representation of the muscle or the nerve is shown. The muscle or nerve is generally represented as a resistor 112. The electrode plus the lead is schematically illustrated by connection point 108. Stimulation capacitor 106 is in series between the lead connection point 108 and the collector of power transistor 110. A switch circuit is connected between the collector of power transistor 110 and the high power voltage VPP. The switch is closed in inactive mode (no stimulation, no test) to allow the stimulation capacitor 106 to be discharged through the impedance path (108,112).

The switch is open in stimulation or testing mode, and a controlled current is sunk through the power transistor 110 during a calibrated time window "STI" as previously explained. The capacitor is thus charged at a constant current I. In a preferred embodiment, the high power voltage is 40V in order to get a sufficient current (>20 mA) to the muscle, which offers a resistive value in the range of 1500 ohms.

To restate, the principle of impedance testing is to detect if a current is flowing from the muscle or nerve through the stimulation capacitor Cs. If the electrode is connected to the muscle (or the nerve) there is a current flowing in the muscle (or the nerve), but if no current is flowing it means that the electrode is disconnected from the muscle (or the nerve) or broken.

Figure 4:
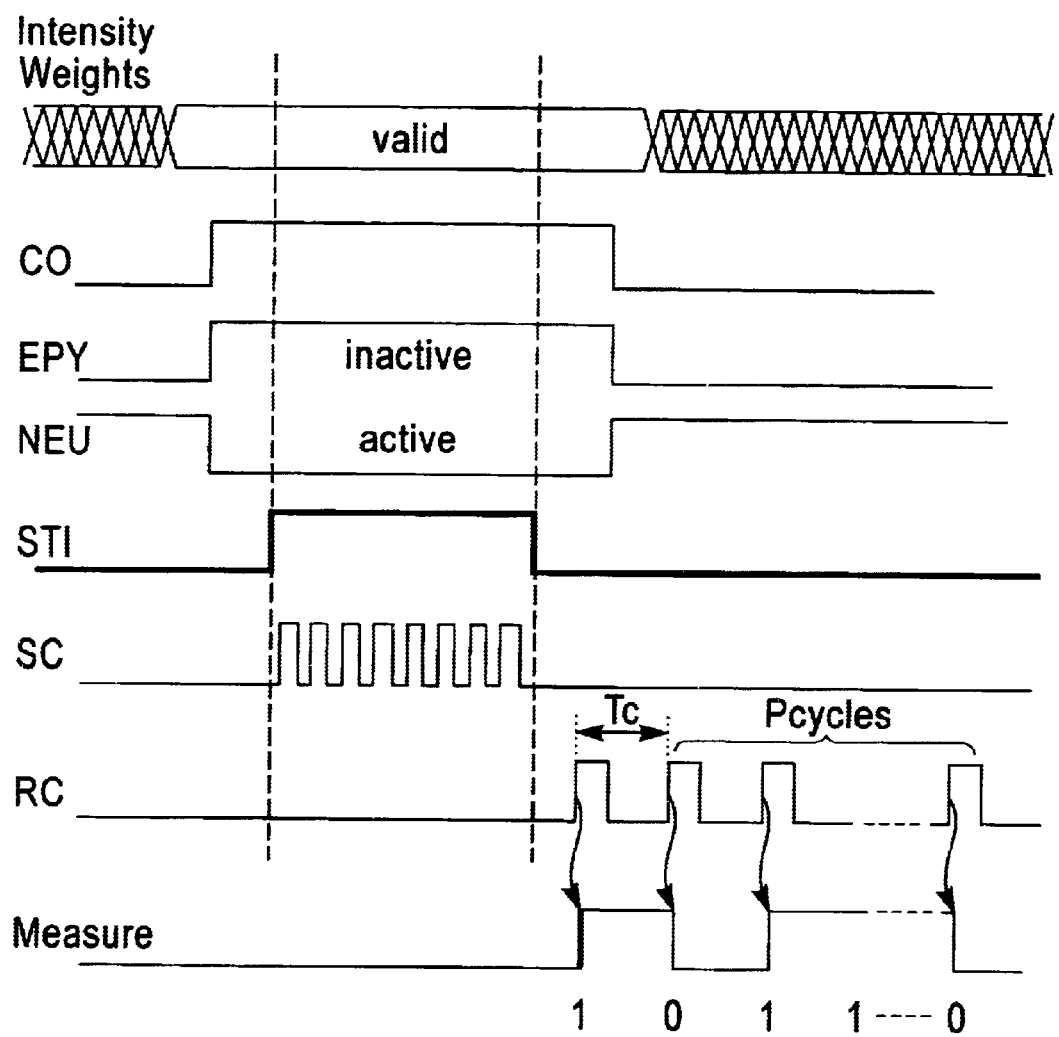
FIG. 4 is a timing diagram representing the main signals flowing in the circuits of FIG. 2.

Reference is now made to the timing diagram of FIG. 4. To operate in test mode the circuit of the invention, a DC current is first determined by the settings of the intensity weights on the D/A converter inputs, which are validated by the "CO" command.

Then the type of stimulation is selected by activation of one of the selection signals "EPY" or "NEU". The stimulation signal "STI" is generated on the output of the control circuit and one power transistor 110 becomes active as already explained. During the duration of the stimulation signal "STI", the sampling clock "SC" is running in order to convert the emitter voltage of the active power transistor 110 into P-binary data. Finally, the P-binary data are stored into a P-bits register 206. The stored data are then serially outputted as shown on last line "MEASURE" of FIG. 4 during P clock cycles "RC". The output pattern is thus representative of the voltage emitter status.

One advantage the solution is that the test is completely performed internally to the implantable device. Other advantages include that only a few devices are required, no extra I/Os are required for the ASIC, and no extra feed through wires for the implant are required. Still other advantages include no extra external components are required for the implant, implant is simpler (no extra wiring), the power consumption is optimized (the ASIC is low powered), there is no limitation of the number of lead connections, and the solution offers flexibility on the timings as the impedance test can be performed either during a normal stimulation or during a test mode without any stimulation of the muscle or the nerve.

It is to be understood that the provided illustrative examples are by no means exhaustive of the many possible uses for my invention.

From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims:

What is claimed is:

1. An apparatus for testing the impedance of a medical lead connecting an implantable stimulation device to one of either a nerve or a muscle, the implantable device comprising capacitor for stimulating the nerve or the muscle, said apparatus comprising:

a current generator for generating a testing current 'I' during a calibrated testing pulse 'STI', said current generator comprising a pulse generator for generating the calibrated testing pulse; and a power circuit coupled to the capacitor and to the current generator for determining if the capacitor is charged by the testing current during the calibrated testing pulse.

2. The apparatus of claim 1 wherein the current generator comprises at least one D/A converter (200).

3. The apparatus of claim 1 wherein the current generator is a low powered device operating in the range of five volts.

4. The apparatus of claim 1 wherein the current generator for generating a testing current "I" during a calibrated testing pulse "STI" is implemented within a low power ASIC.

5. The apparatus of claim 1 wherein the power circuit is a transistor device coupled to the output of the pulse generator.

6. The apparatus of claim 5 wherein the transistor device is a power transistor for adapting the low voltage calibrated testing pulse "STI" to the high power voltage of the capacitor.

7. The apparatus of claim 5 further comprising a measuring device connected to the output of the transistor device for measuring the transistor output voltage.

8. The apparatus of claim 7 wherein the measuring device comprises an A/D converter for converting the output voltage of the transistor device into binary bits.

9. The apparatus of claim 8 further comprising a register connected to the output of the A/D converter for storing the binary bits.

* * * * *